(12) United States Patent
Costello et al.

(10) Patent No.: US 7,390,427 B2
(45) Date of Patent: *Jun. 24, 2008

(54) HYDROFLUOROETHER AS A HEAT-TRANSFER FLUID

(75) Inventors: Michael G. Costello, Afton, MN (US); Richard M. Flynn, Mahtomedi, MN (US); Frederick E. Behr, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/536,091

(22) Filed: Sep. 28, 2006

(65) Prior Publication Data

US 2007/0018134 A1    Jan. 25, 2007

Related U.S. Application Data

(62) Division of application No. 10/738,887, filed on Dec. 16, 2003, now Pat. No. 7,128,133.

(51) Int. Cl.
*C09K 5/10* (2006.01)
*F28C 3/00* (2006.01)

(52) U.S. Cl. ............... 252/68; 252/70; 252/78.1; 252/570; 165/80.4; 165/80.5; 165/104.33; 568/683; 429/62; 363/13; 257/48; 257/798

(58) Field of Classification Search ............ None
See application file for complete search history.

(56) References Cited

U.S. PATENT DOCUMENTS

| | | |
|---|---|---|
| 3,362,180 A | 1/1968 | Eiseman, Jr. |
| 3,549,711 A | 12/1970 | Merrill et al. |
| 3,739,033 A | 6/1973 | Anello et al. |
| 3,962,348 A | 6/1976 | Benninger et al. |
| 4,079,084 A | 3/1978 | Houghton |
| 5,713,211 A | 2/1998 | Sherwood |
| 5,750,797 A | 5/1998 | Vitcak et al. |
| 5,847,048 A | 12/1998 | Feiring |
| 5,925,611 A | 7/1999 | Flynn et al. |
| 6,205,799 B1 | 3/2001 | Patel et al. |
| 6,280,808 B1 | 8/2001 | Fields et al. |
| 6,297,308 B1 | 10/2001 | Jariwala et al. |
| 6,303,080 B1 | 10/2001 | Tuma |
| 6,347,907 B1 | 4/2002 | Tousignant et al. |
| 6,429,400 B1 | 8/2002 | Sawada et al. |
| 6,746,620 B2 | 6/2004 | Maccone et al. |
| 6,866,094 B2 | 3/2005 | Cousineau et al. |

FOREIGN PATENT DOCUMENTS

| | | |
|---|---|---|
| FR | 2 287 432 | 5/1976 |
| GB | 1 354 138 | 5/1974 |
| JP | 62-103034 | 5/1987 |
| RU | 1810324 A | 4/1993 |
| WO | WO 02/102858 | 12/2002 |

OTHER PUBLICATIONS

Aldrich et al., "α-Fluorinated Ethers. II. Alkyl Fluoroalkyl Ethers", *J. Org. Chem.*, 29(1) 11-15 (1964).
Blazejewski et al., "Sythesis of 2-trifluoromethoxyethyl trifluoromethoxyacetate and derived 2-trifluoromethoxyacrylates", *J. Fluorine. Chem.*, 117(2) 161-166 (2002).
Chi et al., "A Facile Synthesis of Partly-fluorinated Ethers Using Perfluoropropoxyethylene and Aliphatic Alcohols", *Bull. Korean Chem Soc.*, 20(2) 220-222 (1999).
Sievert et al., "Synthesis of Perfluorinated Ethers by an Improved Solution Phase Direct Fluorination Process", *J. Fluorine Chem.*, 53, 397-417 (1991).
Sherwood, "Secondary Heat Transfer Systems and the Application of a New Hydrofluoroether", presented at the International CFC & Halon Alternatives Conference, Washington, DC, Oct. 1995, 11 pages.

*Primary Examiner*—Necholus Ogden
(74) *Attorney, Agent, or Firm*—Dean M. Harts; Stephan F. Wolf

(57) ABSTRACT

The present invention provides an apparatus comprising a device and a mechanism for heat transfer comprising a hydrofluoroether heat-transfer fluid wherein the heat transfer fluid is represented by the following structure:

$$R_f\text{—O—}R_h\text{—O—}R_f'$$

wherein O is oxygen; $R_f$ and $R_f'$ are, independently, a fluoroaliphatic group, wherein each $R_f$ and $R_f'$ contain 1 hydrogen atom; $R_h$ is independently a linear, branched or cyclic alkylene group having from 2 to about 8 carbon atoms and at least 4 hydrogen atoms, and wherein the hydrofluoroether compound is free of —O—$CH_2$—O—. Another embodiment of the present invention is a method therefor.

14 Claims, No Drawings

HYDROFLUOROETHER AS A HEAT-TRANSFER FLUID

CROSS REFERENCE TO RELATED APPLICATIONS

This application is a divisional of U.S. Ser. No. 10/738,887, filed Dec. 16, 2003 now U.S. Pat. No. 7,128,133, now allowed, the disclosure of which is incorporated by reference in its entirety herein.

FIELD OF INVENTION

This invention relates to hydrofluoroether fluids and their use as heat-transfer fluids.

BACKGROUND

Presently various fluids are used for heat transfer. The suitability of the heat-transfer fluid depends upon the application process. For example, some electronic applications require a heat-transfer fluid which is inert, has a high dielectric strength, has low toxicity, good environmental properties, and good heat transfer properties over a wide temperature range. Other applications require precise temperature control and thus the heat-transfer fluid is required to be a single phase over the entire process temperature range and the heat-transfer fluid properties are required to be predictable, i.e., the composition remains relatively constant so that the viscosity, boiling point, etc. can be predicted so that a precise temperature can be maintained and so that the equipment can be appropriately designed.

In the semiconductor industry, there are numerous devices or processes that require a heat-transfer fluid having select properties. The heat-transfer fluid may be used to remove heat, add heat, or maintain a temperature.

Each of the semiconductor processes described below incorporates a device or a work-piece which has heat removed from it or has heat added to it. The heat transfer associated with either the heat removal or addition can take place over a wide temperature range. Thus, in each case a heat-transfer fluid is preferably used which has other attributes that make it "operator friendly". In order for a heat-transfer fluid to be considered "operator friendly", the heat-transfer fluid preferably exhibits low toxicity and low flammability.

For automated test equipment (ATE), equipment is used to test the performance of semiconductor dice. The dice are the individual "chips" that are cut from a wafer of semiconductor substrate. The dice come from the semiconductor foundry and must be checked to ensure they meet functionality requirements and processor speed requirements. The test is used to sort "known good dice" (KGD) from dice that do not meet the performance requirements. This testing is generally performed at temperatures ranging from about −80° C. to about 100° C.

In some cases the dice are tested one-by-one, and an individual die is held in a chuck. This chuck provides, as part of its design, provision for cooling the die. In other cases, several dice are held in the chuck and are tested either sequentially or in parallel. In this situation, the chuck provides cooling for several dice during the test procedure.

It may also be advantageous to test dice at elevated temperatures to determine their performance characteristics under conditions of elevated temperature. In this case, a coolant which has good heat-transfer properties well above room temperature is advantageous.

In some cases, the dice are tested at very low temperatures. For example, Complementary Metal-Oxide Semiconductor ("CMOS") devices in particular operate more quickly at lower temperatures.

If a piece of ATE equipment employs CMOS devices "on board" as part of its permanent logic hardware, it may be advantageous to maintain the logic hardware at a low temperature.

Therefore, to provide maximum versatility to the ATE, a heat-transfer fluid preferably performs well at both low and high temperatures (i.e., preferably has good heat transfer properties over a wide temperature range), is inert (i.e., is non-flammable, low in toxicity, non-chemically reactive), has high dielectric strength, has a low environmental impact, and has predictable heat-transfer properties over the entire operating temperature range.

Etchers operate over temperatures ranging from about 70° C. to about 150° C. In this process, reactive plasma is used to anisotropically etch the features in a wafer. The wafers to be processed are kept at a constant temperature at each selected temperature. Therefore, the heat-transfer fluid preferably is a single phase over the entire temperature range. Additionally, the heat-transfer fluid preferably has predictable performance over the entire range so that the temperature can be precisely maintained.

Ashers operate over temperatures ranging from about 40° C. to about 150° C. This is a process that removes the photosensitive organic "mask".

Steppers operate over temperatures ranging from about 40° C. to about 80° C. This is the process step in semiconductor manufacturing where the reticules needed for manufacturing are produced. Reticules are used to produce the patterns of light and shadow needed to expose the photosensitive mask. The film used in the steppers is typically maintained within a temperature window of +/−0.2° C. to maintain good performance of the finished reticule.

PECVD (plasma enhanced chemical vapor deposition) chambers operate over temperatures ranging from about 50° C. to about 150° C. In this process, films of silicon oxide, silicon nitride, and silicon carbide are grown on a wafer by the chemical reaction initiated in a reagent gas mixture containing silicon and either: 1) oxygen; 2) nitrogen; or 3) carbon. The chuck on which the wafer rests is kept at a uniform, constant temperature at each selected temperature.

Heat-transfer fluids which are presently used in these semiconductor applications include perfluorocarbons (PFCs), perfluoropolyethers (PFPEs), perfluoroamines (PFAs), perfluoroethers (PFEs), water/glycol mixtures, deionized water, silicone oils and hydrocarbon oils. However, each of these heat-transfer fluids has some disadvantage. PFCs, PFPEs, PFAs and PFEs may exhibit atmospheric lifetime values of greater than 500 years, and up to 5,000 years. Additionally, these materials may exhibit high global warming potentials ("GWP"). GWP is the integrated potential warming due to the release of one (1) kilogram of sample compound relative to the warming due to one (1) kilogram of $CO_2$ over a specified integration time horizon. Water/glycol mixtures are temperature limited, that is, a typical low temperature limit of such mixtures is −40° C. At low temperatures water/glycol mixtures also exhibit relatively high viscosity. The high viscosity at low temperature yields high pumping power. Deionized water has a low temperature limit of 0° C. Silicone oils and hydrocarbon oils are typically flammable.

Removing heat from electronic devices has become one of the most important obstacles to further improving processor performance. As these devices become more powerful, the amount of heat generated per unit time increases. Therefore, the mechanism of heat transfer plays an important role in processor performance. The heat-transfer fluid preferably has good heat transfer performance, good electrical compatibility (even if used in "indirect contact" applications such as those employing cold plates), as well as low toxicity, low (or non-) flammability and low environmental impact. Good electrical compatibility requires the heat-transfer fluid candidate to exhibit high dielectric strength, high volume resistivity, and poor solvency for polar materials. Additionally, the heat-transfer fluid candidate must exhibit good mechanical compatibility, that is, it must not affect typical materials of construction in an adverse manner. In this application, heat-transfer fluid candidates are disqualified if their physical properties are not stable over time.

Materials currently used as heat-transfer fluids for cooling electronics or electrical equipment include PFCs, PFPEs, silicone oils, and hydrocarbon oils. Each of these heat-transfer fluids has some disadvantage. PFCs and PFPEs may be environmentally persistent. Silicone oils and hydrocarbon oils are typically flammable.

Thermal shock testing is generally performed at temperatures ranging from about −65° C. to about 150° C. The rapid cycling of temperature in a part or device may be required to simulate the thermal changes brought on by, for instance, launching a missile. Thermal shock testing is required for electronics used for military missiles, among other things. There are several military specifications related to thermal shock testing of many electronic components and assemblies. This test uses various means of imparting rapidly changing temperatures within a part or electronic device. One such device employs a liquid heat-transfer fluid or liquid heat-transfer fluids that are kept in separate reservoirs maintained at temperature extremes where parts are alternately immersed to induce thermal shock to the test part. Typically, operators load and unload the components or assemblies to and from the thermal shock equipment. Therefore, it is important that a heat-transfer fluid used in such an application exhibit low toxicity, low flammability, and low environmental impact. Heat-transfer fluids which are liquid over a wide temperature range coupled with low toxicity, low flammability, and low environmental impact are ideal for thermal shock testing.

Materials currently used as heat-transfer fluids for liquid/liquid thermal shock test baths include liquid nitrogen, PFCs, and PFPEs. Each of these heat-transfer fluids has some disadvantage. Liquid nitrogen systems offer limited temperature selectivity at the low temperature end. PFCs and PFPEs may be environmentally persistent.

Constant temperature baths are typically operated over a broad temperature range. Therefore, desirable heat-transfer fluids preferably have a wide liquid range and good low-temperature heat transfer characteristics. A heat-transfer fluid having such properties allows a very wide operating range for the constant temperature bath. Typically, most testing fluids require fluid change-out for wide temperature extremes. Also, good temperature control is essential for accurately predicting physical properties of the heat-transfer fluids.

Heat-transfer fluids which are presently used in this application include: perfluorocarbons (PFCs), perfluoropolyethers (PFPEs), water/glycol mixtures, deionized water, silicone oils, hydrocarbon oils, and hydrocarbon alcohols. Each of these heat-transfer fluids has some disadvantage. PFCs and PFPEs may be environmentally persistent. Water/glycol mixtures are temperature limited, that is, a typical low temperature limit of such mixtures is −40° C. At low temperatures water/glycol mixtures also exhibit relatively high viscosity. Deionized water has a low temperature limit of 0° C. Silicone oils, hydrocarbon oils and hydrocarbon alcohols are typically flammable.

For heat-transfer processing requiring an inert fluid, fluorinated materials are often used. Fluorinated materials typically have low toxicity, are essentially non-irritating to the skin, are non-chemically reactive, are non-flammable, and have high dielectric strength. Fluorinated materials such as perfluorocarbons, perfluoropolyethers, and hydrofluoroethers provide the additional advantage of not depleting the ozone layer in the stratosphere.

As discussed above, perfluorocarbons, perfluoropolyethers, and some hydrofluoroethers have been used for heat-transfer.

Perfluorocarbons (PFCs) exhibit several traits advantageous to the applications discussed above. PFCs have high dielectric strength and high volume resistivity. PFCs are non-flammable and are generally mechanically compatible with materials of construction, exhibiting limited solvency. Additionally, PFCs generally exhibit low toxicity and good operator friendliness. PFCs are manufactured in such a way as to yield a product that has a narrow molecular weight distribution. They do exhibit one important disadvantage, however, and that is long environmental persistence.

Perfluoropolyethers (PFPEs) exhibit many of the same advantageous attributes described for PFCs. They also have the same major disadvantage, i.e., long environmental persistence. In addition, the methods developed for manufacturing these materials yield products that are not of consistent molecular weight and thus are subject to performance variability.

Hydrofluoropolyethers (HFPEs), a class of hydrofluoroethers (HFEs), exhibit some of the same advantageous attributes of PFCs, but differ greatly in two areas. To their credit, they exhibit markedly lower environmental persistence, yielding atmospheric lifetimes on the order of decades rather than millennia. However, some of the HFPEs taught as heat-transfer fluids are a mixture of components of widely disparate molecular weight. Thus, their physical properties may change over time which makes it difficult to predict performance.

Some hydrofluoroethers have been disclosed as heat-transfer fluids. However, the need exists for a heat-transfer fluid which is inert, has high dielectric strength, low electrical conductivity, chemical inertness, thermal stability and effective heat transfer, is liquid over a wide temperature range, has good heat-transfer properties over a wide range of temperatures and also has a shorter atmospheric lifetime, and therefore a lower global warming potential, than existing heat-transfer fluids.

SUMMARY

In one aspect, the present invention comprises a hydrofluoroether heat-transfer fluid which is inert, has high dielectric strength, low electrical conductivity, chemical inertness, thermal stability and effective heat transfer. Additionally, the present invention comprises a heat transfer fluid that is liquid over a wide temperature range, and has good heat-transfer properties over a wide range of temperature.

In another aspect, the present invention comprises an apparatus requiring heat-transfer comprising a device, and a mechanism for transferring heat to or from the device, comprising using a heat-transfer fluid, wherein the heat transfer fluid is represented by the following structure:

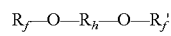

wherein:
O is oxygen;
$R_f$ and $R_f'$ are, independently, a fluoroaliphatic group, wherein each $R_f$ and $R_f'$ contain 1 hydrogen atom;
$R_h$ is independently a linear, branched or cyclic alkylene group having from 2 to about 8 carbon atoms and at least 4 hydrogen atoms, wherein $R_h$ can contain one or more catenated heteroatoms, and
wherein the hydrofluoroether compound is free of formal linkage ("—O—CH$_2$—O—").

Another aspect of the present invention is a method for transferring heat comprising the steps of: providing a device, providing a mechanism for transferring heat comprising a heat-transfer fluid, and using the heat-transfer fluid to transfer heat to or from the device, wherein the heat-transfer fluid is represented by the following structure:

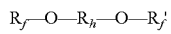

wherein:
O is oxygen;
$R_f$ and $R_f'$ are, independently, a fluoroaliphatic group, wherein each $R_f$ and $R_f'$ contain 1 hydrogen atom;
$R_h$ is independently a linear, branched or cyclic alkylene group having from 2 to about 8 carbon atoms and at least 4 hydrogen atoms, wherein $R_h$ can contain one or more catenated heteroatoms, and
wherein the hydrofluoroether compound is free of —O—CH$_2$—O—.

DETAILED DESCRIPTION

The present invention provides a hydrofluoroether compound, as well as an apparatus and a method for heat-transfer using the hydrofluoroether compound as a heat-transfer fluid. The apparatus of the present invention comprises a device and a mechanism for transferring heat comprising a heat-transfer fluid.

Inert means, for the purpose of the present application, generally not chemically reactive under normal conditions of use.

Hydrofluoroether Compound

The present application describes a hydrofluoroether compound and the use of the hydrofluoroether compound as a heat-transfer fluid. The hydrofluoroether compound is used to heat, cool, and/or maintain the temperature of the device at a select temperature. The hydrofluoroether compound is inert, non-flammable, and environmentally acceptable. Additionally, the hydrofluoroether compound of the present invention exhibits low viscosity throughout the liquid range, and has good heat transfer properties over a wide temperature range.

The hydrofluoroether compound of the present invention is represented by the following structure:

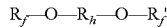

wherein:
O is oxygen
$R_f$ and $R_f'$ are, independently, a fluoroaliphatic group, wherein each $R_f$ and $R_f'$ contain 1 hydrogen atom. $R_f$ and $R_f'$ are stable, inert, non-polar, preferably saturated, monovalent moieties which are both oleophobic and hydrophobic. In some embodiments, $R_f$ and $R_f'$ may contain chlorine. $R_f$ and $R_f'$ generally contain at least about 2 carbon atoms, for example about 3 to about 20 carbon atoms, and in specific embodiments from about 3 to about 7 carbon atoms. $R_f$ and $R_f'$ can contain straight chain, branched chain, or cyclic fluorinated alkylene groups or combinations thereof with straight chain, branched chain, or cyclic alkylene groups. $R_f$ and $R_f'$ are generally free of polymerizable olefinic unsaturation and can optionally contain catenated heteroatoms such as divalent oxygen, or trivalent nitrogen (e.g. C$_3$F$_7$OCFHCF$_2$.) The $R_f$ and $R_f'$ groups may contain at least 3 fluorine atoms, for example at least 4 fluorine atoms, and in some embodiments at least 6 fluorine atoms (e.g., CF$_3$CFHCF$_2$, HCF$_2$CF$_2$, CFClHCF$_2$, (C$_2$F$_5$)(CF$_3$CFH)CF, or the like). Fluoroaliphatic groups with one hydrogen (e.g., those of the formula C$_x$F$_{2x}$H, where x is about 2 to about 8, for example 3 or 4) are examples of embodiments of $R_f$ and $R_f'$.

$R_h$ is independently a linear, branched or cyclic alkylene group having from 2 to about 8 carbon atoms and at least 4 hydrogen atoms, wherein $R_h$ can contain one or more catenated heteroatoms. Examples of $R_h$ include alkylenes, fluoroalkylenes, and the like.

Wherein the hydrofluoroether compound is free of —O—CH$_2$—O—.

The hydrofluoroether compounds of the present invention generally are inert. Additionally, the compounds of the present invention have high dielectric strength and low electrical conductivity. The compounds additionally are thermally stable.

The hydrofluoroether compounds of the present invention are useful as heat transfer liquids. The compounds generally exhibit a liquid phase over a wide temperature range. For example, the compounds are generally liquid to at least about −50° C. Generally, the viscosity of the compounds in the liquid phase is less than 100 centistokes (100×10$^{-6}$ m$^2$/s) at −50° C., preferably less than 50 centistokes (100×10$^{-6}$ m$^2$/s).

The hydrofluoroether compounds of the present invention additionally have low global warming potential values (GWP), in some embodiments under 500. GWP is determined using a calculated value for atmospheric lifetime and an experimentally determined infrared absorbance data integrated over the spectral region of interest, typically 500 to 2500 cm$^{-1}$. A detailed description of GWP can be found, for example in U.S. Pat. No. 5,925,611, which is incorporated by reference.

The hydrofluoroether compounds of the present invention are generally prepared by reaction of a fluorine containing olefin with a difunctional alcohol using potassium carbonate as a catalyst.

Apparatus

In certain embodiments, the invention includes an apparatus requiring heat transfer. The apparatus comprises a device and a mechanism for transferring heat to or from the device using a heat-transfer fluid. Such apparatus include refrigeration systems, cooling systems, testing equipment, and machining equipment.

Examples of an apparatus of the present invention include, but are not limited to, test heads used in automated test equipment for testing the performance of semiconductor dice; wafer chucks used to hold silicon wafers in ashers, steppers, etchers, PECVD tools; constant temperature baths, and thermal shock test baths.

Device

In certain embodiments, the present invention comprises a device. The device is defined herein as a component, workpiece, assembly, etc. to be cooled, heated or maintained at a selected temperature. Such devices include electrical components, mechanical components and optical components. Examples of devices of the present invention include, but are not limited to microprocessors, wafers used to manufacture semiconductor devices, power control semiconductors, electrical distribution switch gear, power transformers, circuit boards, multi-chip modules, packaged and unpackaged semiconductor devices, chemical reactors, nuclear reactors, fuel cells, lasers, and missile components.

Heat Transfer Mechanism

In certain embodiments, the present invention comprises a mechanism for transferring heat. Heat is transferred by placing the heat transfer mechanism in thermal contact with the device. The heat transfer mechanism, when placed in thermal contact with the device, removes heat from the device or provides heat to the device, or maintains the device at a selected temperature. The direction of heat flow (from device or to device) is determined by the relative temperature difference between the device and the heat transfer mechanism.

The heat transfer mechanism comprises the heat-transfer fluid of the present invention.

Additionally, the heat transfer mechanism may include facilities for managing the heat-transfer fluid, including, but not limited to: pumps, valves, fluid containment systems, pressure control systems, condensers, heat exchangers, heat sources, heat sinks, refrigeration systems, active temperature control systems, and passive temperature control systems.

Examples of suitable heat transfer mechanisms include, but are not limited to, temperature controlled wafer chucks in PECVD tools, temperature controlled test heads for die performance testing, temperature controlled work zones within semiconductor process equipment, thermal shock test bath liquid reservoirs, and constant temperature baths.

In some systems, such as etchers, ashers, PECVD chambers, thermal shock testers, the upper desired operating temperature may be as high as 150° C.

Method

The present invention additionally comprises a method for transferring heat comprising the steps of: providing a device, providing a mechanism for transferring heat comprising a heat-transfer fluid, and using the heat-transfer fluid to transfer heat to or from the device, wherein the heat-transfer fluid is represented by the following structure:

$$R_f\text{—}O\text{—}R_h\text{—}O\text{—}R_f'.$$

EXAMPLES

The present invention will be further described with reference to the following nonlimiting examples and test methods. All parts, percentages, and ratios are by weight unless otherwise specified.

Example 1

Preparation of 1,1,1,2,3,3-Hexafluoro-3-[2-(1,1,2,3,3-hexafluoro-propoxy)-ethoxy]-propane ($CF_3CFHCF_2OCH_2CH_2OCF_2CFHCF_3$)

Into a clean dry 600 mL Parr reactor equipped with stirrer, heater and thermocouple were added 16.8 g (0.12 mol) of potassium carbonate, 40.0 g (0.64 mol) of ethylene glycol and 200 mL of anhydrous acetonitrile. The reactor was sealed and heated to 30° C. Over a period of 4.25 hours, 208 g of hexafluoropropene (available from Aldrich) was added to the reactor. The temperature was maintained at 30° C. during the addition of the $C_3F_6$ and the pressure kept under 40 psig (276 kPa). At the end of the addition, the reactor was heated to 40° C. and held 20 minutes. The reactor contents were then allowed to cool and excess pressure was vented. The reactor contents were added to a 1-L separatory funnel and water washed three times. The lower phase was dried with magnesium sulfate, filtered and fractionally distilled in a concentric tube fractionating unit (Ace Glass Catalog Number 9331) to provide 95 g of 95.3% purity $CF_3CFHCF_2OC_2H_4OCF_2CFHCF_3$. The sample also contained 3.6% of olefins formed by HF removal from the desired compound. The sample was then shaken with anhydrous HF, phase split, water washed and dried with anhydrous magnesium sulfate to give 99.5% pure 1,1,1,2,3,3-Hexafluoro-3-[2-(1,1,2,3,3,3-hexafluoro-propoxy)-ethoxy]-propane. The boiling point was 164° C. and the structures were confirmed by gas chromatography-mass spectrography (gc-ms). The viscosity was 27 centistokes ($27 \times 10^{-6}$ m$^2$/s) at −50° C. measured using a Cannon-Fenske viscometer and a Wescan Model 221 viscosity timer.

Example 2

Preparation of 1,1,1,2,3,3-Hexafluoro-3-[3-(1,1,2,3,3,3-hexafluoro-propoxy)-propoxy]-propane ($CF_3CFHCF_2OC_3H_6OCF_2CFHCF_3$)

1,3-propanediol (30 g, 0.39 mole, Aldrich), potassium carbonate (10 g, 0.073 mole) and acetonitrile (120 mL,) were combined in a 600 mL Parr reactor. The reactor was sealed and heated to about 32° C. while hexafluoropropene (127 g, 0.844 mole) was added over a period of about six hours. The reactor was cooled and the contents transferred to a 1 L beaker and washed with water. The lower fluorochemical phase was separated and washed with a dilute solution of aqueous sodium chloride. The fluorochemical phase was then distilled in a concentric tube fractionating unit to remove most of the remaining acetonitrile. The residue was then vacuum distilled and a fraction collected with distillation range 55-60° C./3 mmHg. This material was then redistilled in the concentric tube unit and a fraction collected with a boiling point of 188° C. This material consisted of three products as determined by gas chromatography, the desired diether and two products derived from the elimination of HF from the desired product. This was treated with anhydrous HF at ambient temperature and the product washed with water and redistilled under vacuum to give about 60 g of 99.7% pure diether product. The boiling point was 188° C. The viscosity was 35 centistokes ($35 \times 10^{-6}$ m$^2$/s) at −50° C. measured using a Cannon-Fenske viscometer and a Wescan Model 221 viscosity timer.

Example 3

Preparation of 2,2,3,3,4,4-Hexafluoro-1,5-bis(1,1,2,3,3,3-hexafluoro-propoxy)pentane ($CF_3CFHCF_2OCH_2C_3F_6CH_2OCF_2CFHCF_3$)

1,3-hexafluoropentanediol (21.2 g, 0.1 mole, Aldrich), potassium carbonate (2.76 g, 0.02 mole) and acetonitrile (75 mL) were combined in a 600 mL Parr reactor. The reactor was sealed and heated to about 32° C. Hexafluoropropene (34.5 g, 0.23 mole) was added slowly over about five hours at this temperature. The reaction mixture was then allowed to stir for sixteen hours at ambient temperature. The reactor was opened and the contents poured into water, the aqueous solution extracted with diethyl ether and the resulting ether layer separated and washed three times with a low concentration of sodium chloride in water. The ether was removed by rotary evaporation and the product one-plate distilled (65-70° C./3 mmHg). Since the product contained two olefins that were of the same mass as the desired ether with the loss of one mole of HF, the material was treated by addition of anhydrous HF at ambient temperature. In this case, the HF treatment failed to remove the olefinic impurities. The product was then distilled through the concentric tube column. The boiling point was 214° C. and had a purity of 86%.

Example 4

Preparation of 1,1,1,2,2,3,3-Heptafluoro-3-{1,2,2-trifluoro-2-[2-(1,1,2-trifluoro-2-heptafluoropropyloxy-ethoxy)-ethoxy]-ethoxy}-propane ($C_3F_7OCFHCF_2OC_2H_4OCF_2CFHOC_3F_7$)

Perfluoropropylvinyl ether (189.0 g, 0.71 mole, available from SynQuest, Alachula, Fla.), potassium carbonate (10 g, 0.073 mole), ethylene glycol (20.8 g, 0.33 mole) and acetonitrile (200 mL) were combined in a 600 mL Parr reactor. The reactor was sealed and heated to 30° C. for 19 hours. The reactor was cooled and the contents filtered into a 1-L separatory funnel and water washed four times. The fluorochemical phase was dried with anhydrous sodium sulfate, filtered and fractionated in the concentric tube unit to give a fraction boiling at 210° C. and 99.2% purity of the $C_3F_7OCFHCF_2OC_2H_4OCF_2CFHOC_3F_7$. Structure was confirmed by gc-ms. The viscosity was 150 centistokes (150× $10^{-6}$ m$^2$/s) at −50° C. measured using a Cannon-Fenske viscometer and a Wescan Model 221 viscosity timer.

Example 5

Preparation of 1,1,1,2,2,3,3-Heptafluoro-3-{1,2,2-trifluoro-2-[2-(1,1,2,3,3,3-hexafluoro-propoxy)-ethoxy]-ethoxy}propane ($C_3F_7OCFHCF_2OC_2H_4OCF_2CFHCF_3$)

Perfluoropropylvinyl ether (139.0 g, 0.52 mole), potassium carbonate (19.3 g, 0.14 mole), ethylene glycol (155.5 g, 2.5 mole) and acetonitrile (200 mL) were combined in a 600 mL Parr reactor. The reactor was sealed and heated to 30° C. for 2.75 hours. The reaction mixture was filtered and then water washed four times to give 146.4 g of $C_3F_7OCFHCF_2OC_2H_4OH$ (54.2%) and ($C_3F_7OCFHCF_2OCH_2$)$_2$ (43.4%). This material was combined with 179 g from a previous run consisting of 21.6% $C_3F_7OCFHCF_2OC_2H_4OH$ and 76.1% ($C_3F_7OCFHCF_2OCH_2$)$_2$ and fractionated to give a 106.3 g fractionation cut boiling from 167-173° C. of $C_3F_7OCFHCF_2OC_2H_4OH$ (80.8% pure). This material along with potassium carbonate (7.3 g, 0.052 mole) and acetonitrile (200 mL) were added to a 600 mL Parr reactor. The reactor was sealed and heated to 30° C. Hexafluoropropene (48.5 g, 0.32 mole) was added to the reactor over a 30 minute period and the reactor contents were held at 30° C. an additional 40 minutes. The reactor was cooled and the contents filtered into a 1-L separatory funnel and water washed four times, dried with anhydrous sodium sulfate and filtered. The material was shaken with anhydrous HF, water washed, dried with anhydrous sodium sulfate and filtered to give 125.6 g of $C_3F_7OCHFCF_2OC_2H_4OCF_2CFHCF_3$ (86.3% pure). The material was fractionated in the concentric tube unit to give 72.3 g of $C_3F_7OCHFCF_2OC_2H_4OCF_2CFHCF_3$ (95.3% purity) boiling at 194° C. Structure was confirmed by gc-ms. The viscosity was 48 centistokes (48×$10^{-6}$ m$^2$/s) at −50° C. measured using a Cannon-Fenske viscometer and a Wescan Model 221 viscosity timer.

Example 6

Preparation of ($C_2F_5$)($CF_3CFH$)$CFOC_2H_4OCF(CFHCF_3)(C_2F_5)$

Perfluoropentene-2 (69.9 g, 0.28 mole), potassium carbonate (6.0 g, 0.043 mole), ethylene glycol (7.9 g, 0.13 mole) and acetonitrile (200 mL) were combined in a 600 mL Parr reactor. The reactor was heated to 50° C. and held for 16 hours, then heated to 70° C. and held 1 hour. The reactor was cooled and excess pressure vented. The reactor contents were filtered into a 1-L separatory funnel and water washed three times to give 34.6 g of a lower phase. The lower phase was one-plate distilled at atmospheric pressure to a head temperature of 50° C. to remove low boilers. The bottoms of the distillation (19.6 g) were shaken with anhydrous HF, water washed twice, dried with sodium sulfate and filtered to give 6.0 g of mixed isomers of ($C_2F_5$)($CF_3CFH$)$CFOC_2H_4OCF(CFHCF_3)(C_2F_5)$. Structure was confirmed by gc-ms.

Example 7

Preparation of 2-Chloro-1-[2-(2-chloro-1,1,2-trifluoro-ethoxy)-ethoxy]-1,1,2-trifluoro-ethane ($ClHFCCF_2OC_2H_4OCF_2FHCl$)

Ethylene glycol (20.8 g, 0.33 mole, Aldrich), potassium carbonate (9.5 g, 0.069 mole) and acetonitrile (200 mL) were combined in a 600 mL Parr reactor. The reactor was sealed and heated to about 30° C. while chlorotrifluoroethylene (81.0 g, 0.69 mole, available from SynQuest) was added over a period of about two hours. The reaction mixture was then stirred for an additional 16 hours at 30° C. The reactor contents were filtered into a 1-L separatory funnel, water washed five times, dried with anhydrous sodium sulfate and filtered. After fractional distillation using the concentric tube column, a 31.2 g cut was obtained boiling at 200° C. Purity was 99.9% by gas chromatography. Structure was verified by gc-ms. The viscosity was 132 centistokes (132×$10^{-6}$ m$^2$/s) at −50° C. measured using a Cannon-Fenske viscometer and a Wescan Model 221 viscosity timer.

Example 8

Preparation of 1,1,2-Trifluoro-2-trifluoromethoxy-1-[2-(1,1,2-trifluoro-2-trifluoromethoxy-ethoxy)-ethoxy]-ethane ($CF_3OCFHCF_2OC_2H_4OCF_2CFHOCF_3$)

Ethylene glycol (15.7 g, 0.253 mole), potassium carbonate (3.3 g, 0.024 mole) and acetonitrile (100 g) were combined in a 600 mL Parr reactor. The reactor was sealed and heated to about 32° C. while perfluoromethylvinyl ether ($CF_3OCF=CF_2$, 96.7 g, 0.582 mole, available from SynQuest) was added over a period of about four hours. The pressure in the reactor at the end of the addition was 55 psig. The reaction was held at 32° C. for about 64 hours at which time the reactor pressure was 20 psig (139 kPa). The excess pressure was released and the reaction mixture poured into water. The lower fluorochemical phase was separated and washed one time with water. The remaining acetonitrile was removed by distillation through the concentric tube column and the main product fraction collected in a distillation range of 170-172° C. This fraction was combined with an earlier fraction (158-170° C.) and the combined material treated with anhydrous HF as described in previous examples and the resulting product redistilled to give the final product with a boiling point of 170° C. at 97% purity. The viscosity was 30 centistokes ($30 \times 10^{-6}$ m$^2$/s) at $-50°$ C. measured using a Cannon-Fenske viscometer and a Wescan Model 221 viscosity timer.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims as set forth herein as follows.

What is claimed is:

1. A heat-transfer fluid selected from $CF_3CFHCF_2OC_3H_6OCF_2CFHCF_3$, $CF_3OCFHCF_2OC_2H_4OCF_2CFHOCF_3$, $C_3F_7OCFHCF_2OC_2H_4OCF_2CFHCF_3$, $CF_3CFHCF_2OCH_2C_3F_6CH_2OCF_2CFHCF_3$, and mixed isomers of $(C_2F_5)(CF_3CFH)CFOC_2H_4OCF(CFHCF_3)(C_2F_5)$.

2. A method for removing olefinic unsaturation from a heat transfer fluid comprising:
   (a) providing a hydrofluoroether heat-transfer fluid selected from $CF_3CFHCF_2OC_3H_6OCF_2CFHCF_3$, $CF_3OCFHCF_2OC_2H_4OCF_2CFHOCF_3$, $C_3F_7OCFHCF_2OC_2H_4OCF_2CFHCF_3$, $CF_3CFHCF_2OCH_2C_3F_6CH_2OCF_2CFHCF_3$, and mixed isomers of $(C_2F_5)(CF_3CFH)CFOC_2H_4OCF(CFHCF_3)(C_2F_5)$; and
   (b) contacting the heat transfer fluid with anhydrous hydrogen fluoride.

3. A method for transferring heat comprising:
   (a) providing a device; and
   (b) using a heat-transfer fluid to transfer heat to or from the device, wherein the heat-transfer fluid is selected from $CF_3CFHCF_2OC_3H_6OCF_2CFHCF_3$, $C_3F_7OCFHCF_2OC_2H_4OCF_2CFHCF_3$, $CF_3CFHCF_2OCH_2C_3F_6CH_2OCF_2CFHCF_3$, and mixed isomers of $(C_2F_5)(CF_3CFH)CFOC_2H_4OCF(CFHCF_3)(C_2F_5)$.

4. The method of claim 3 further comprising contacting the heat transfer fluid with anhydrous hydrogen fluoride to remove olefinic unsaturation.

5. The method of claim 3 wherein the heat-transfer fluid is selected from $CF_3CFHCF_2OC_3H_6OCF_2CFHCF_3$, $C_3F_7OCFHCF_2OC_2H_4OCF_2CFHCF_3$, $CF_3CFHCF_2OCH_2C_3F_6CH_2OCF_2CFHCF_3$, and mixed isomers of $(C_2F_5)(CF_3CFH)CFOC_2H_4OCF(CFHCF_3)(C_2F_5)$.

6. The method of claim 3 wherein the heat-transfer fluid is selected from $C_3F_7OCFHCF_2OC_2H_4OCF_2CFHCF_3$, $CF_3CFHCF_2OCH_2C_3F_6CH_2OCF_2CFHCF_3$, and mixed isomers of $(C_2F_5)(CF_3CFH)CFOC_2H_4OCF(CFHCF_3)(C_2F_5)$.

7. The method of claim 3 wherein the heat-transfer fluid is selected from $C_3F_7OCFHCF_2OC_2H_4OCF_2CFHCF_3$, $CF_3CFHCF_2OCH_2C_3F_6CH_2OCF_2CFHCF_3$, and mixed isomers of $(C_2F_5)(CF_3CFH)CFOC_2H_4OCF(CFHCF_3)(C_2F_5)$.

8. The method of claim 3 wherein the heat transfer fluid has a viscosity is less than 100 centistokes ($100 \times 10^{-6}$ m$^2$/s) at $-50°$ C.

9. The method of claim 3 wherein the heat transfer fluid has a viscosity of less than 50 centistokes ($50 \times 10^{-6}$ m$^2$/s) at $-50°$ C.

10. The method of claim 3, wherein the device is selected from: microprocessors, wafers used to manufacture semiconductor devices, power control semiconductors, electrical distribution switch gear, power transformers, circuit boards, multi-chip modules, packaged and unpackaged semiconductor devices, chemical reactors, nuclear reactors, fuel cells, lasers, or missile components.

11. The method according to claim 3, wherein the device is heated.

12. The method according to claim 3, wherein the device is cooled.

13. The method according to claim 3, wherein the device is maintained at a selected temperature.

14. The method according to claim 3, wherein the mechanism for transferring heat is selected from temperature controlled wafer chucks in PECVD tools, temperature controlled test heads for die performance testing, temperature controlled work zones within semiconductor process equipment, thermal shock test bath liquid reservoirs, or constant temperature baths.

* * * * *

UNITED STATES PATENT AND TRADEMARK OFFICE
CERTIFICATE OF CORRECTION

PATENT NO.       : 7,390,427 B2                                    Page 1 of 1
APPLICATION NO.  : 11/536091
DATED            : June 24, 2008
INVENTOR(S)      : Michael G. Costello It is certified that error appears in the above-identified patent and that said Letters Patent is hereby corrected as shown below:

Title page, Item [56], References Cited, under Foreign Patent Documents, Entry 4, delete "RU" and insert --SU--, therefor.

Title Page, Item [56], References Cited, under Other Publications, Entry 2, delete "Sythesis" and insert --Synthesis--, and delete "Fluorine." and insert --Fluorine--, therefor.

Column 2,
Line 56, delete "CO2" and insert --$CO_2$--, therefor.

Column 5,
Line 57, after "oxygen" insert --,--.

Column 9,
Line 14, delete "Alachula" and insert --Alachua--, therefor.

Column 11,
Line 18, Claim 1, delete "and" and insert --or--, therefor.

Column 12,
Line 16, Claim 8, delete "is" and insert --of--, therefor.

Signed and Sealed this

Seventeenth Day of March, 2009

JOHN DOLL
*Acting Director of the United States Patent and Trademark Office*